(12) United States Patent
Evans

(10) Patent No.: US 7,129,510 B2
(45) Date of Patent: Oct. 31, 2006

(54) OPTICAL SENSORS

(75) Inventor: Alan F Evans, Beaver Dams, NY (US)

(73) Assignee: Corning Incorporated, Corning, NY (US)

(*) Notice: Subject to any disclaimer, the term of this patent is extended or adjusted under 35 U.S.C. 154(b) by 5 days.

(21) Appl. No.: 10/978,134

(22) Filed: Oct. 29, 2004

(65) Prior Publication Data

US 2006/0091303 A1 May 4, 2006

(51) Int. Cl.
*G01N 15/06* (2006.01)
*G02B 6/00* (2006.01)
*G02B 6/36* (2006.01)
*G02B 6/04* (2006.01)

(52) U.S. Cl. .......................... 250/573; 385/12; 385/53; 385/115

(58) Field of Classification Search ........... 250/227.27, 250/573, 574, 900, 904; 385/125, 53, 12, 385/115, 116, 136
See application file for complete search history.

(56) References Cited

U.S. PATENT DOCUMENTS

| 5,982,174 | A  | * | 11/1999 | Wagreich et al. ......... 324/244.1 |
| 6,260,614 | B1 | * | 7/2001  | Guy ............................ 165/185 |
| 6,757,464 | B1 | * | 6/2004  | Rubino, Jr. .................. 385/52 |
| 2003/0152308 | A1 | * | 8/2003 | Dhadwal et al. .............. 385/12 |
| 2003/0174986 | A1 | * | 9/2003 | Forbes et al. ............... 385/125 |

* cited by examiner

*Primary Examiner*—Georgia Epps
*Assistant Examiner*—Don Williams
(74) *Attorney, Agent, or Firm*—Ronald J. Paglierani; Tina N. Thompson

(57) ABSTRACT

An optical sensor comprises at least one bundle comprising a plurality of optical fibers and a plurality of separate fluid-tight longitudinally extending ducts; and fluid connectors for introducing fluids selectively into at least some of said ducts. Test cells are formed (a) by array members with a pattern of holes or recesses applied to the end of the bundle, or sandwiched between the ends of two bundles or (b) within the fibers in cases where a duct overlaps with the optical field of the fiber. Usually others of the ducts serve to remove fluid from the test cells.

29 Claims, 11 Drawing Sheets

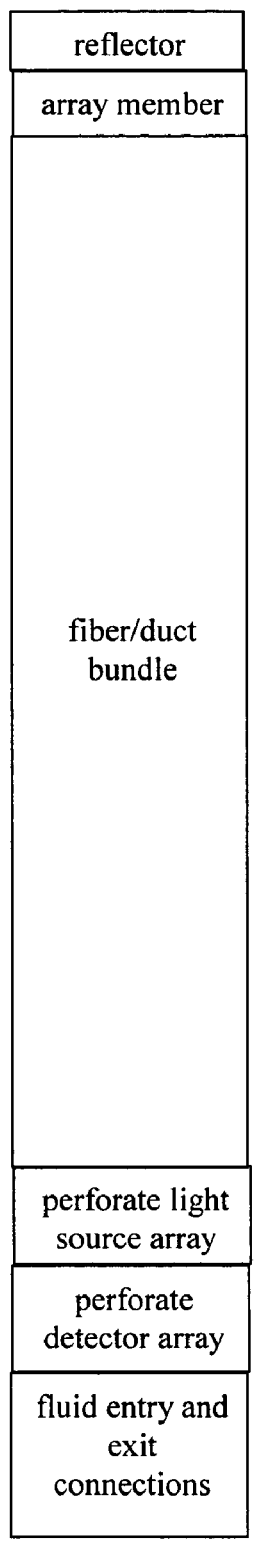
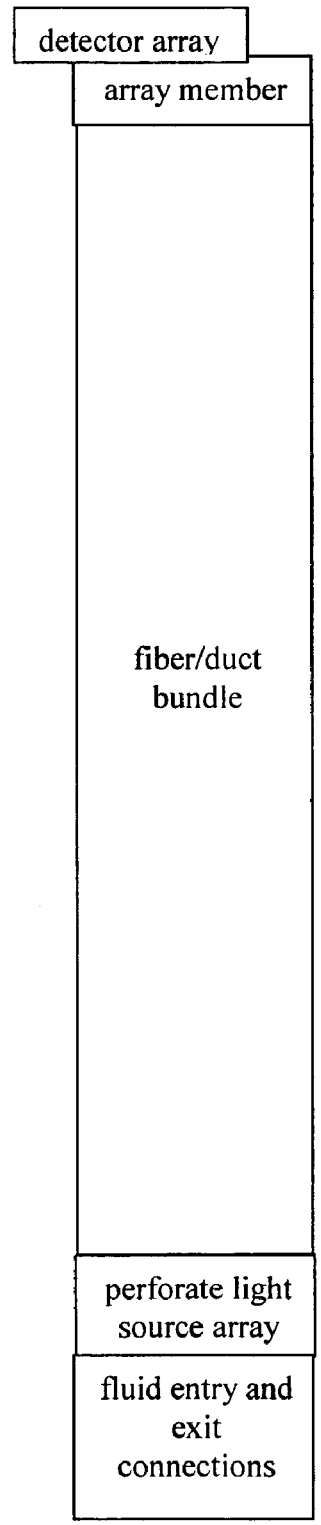
FIG 15
FIG 16

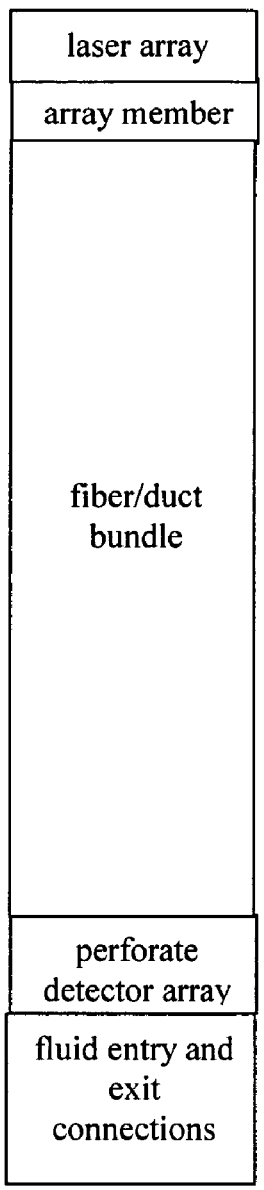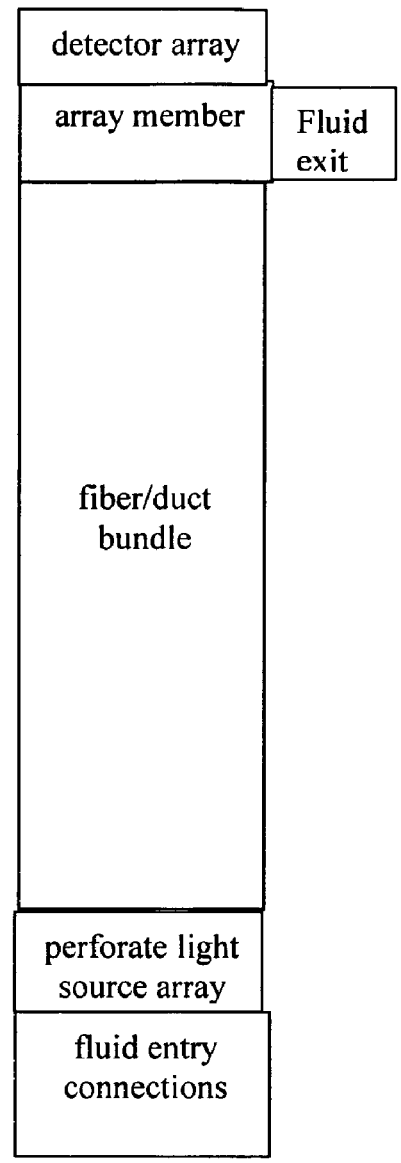
FIG 17                    FIG 18

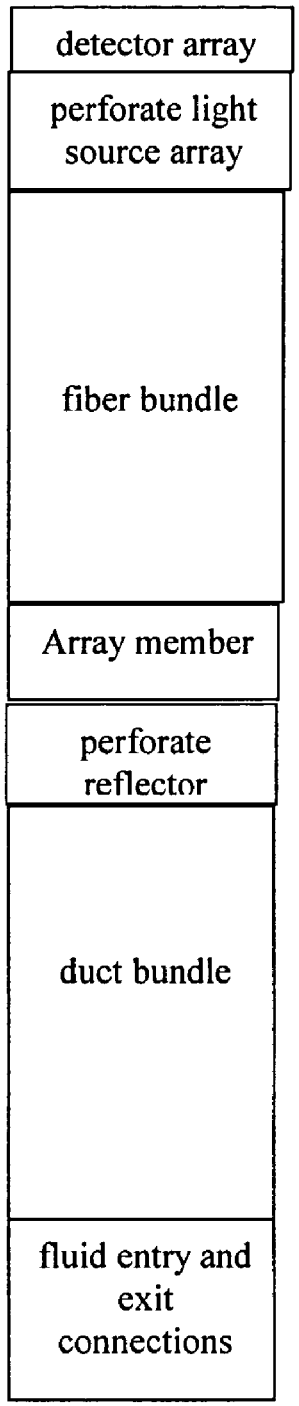
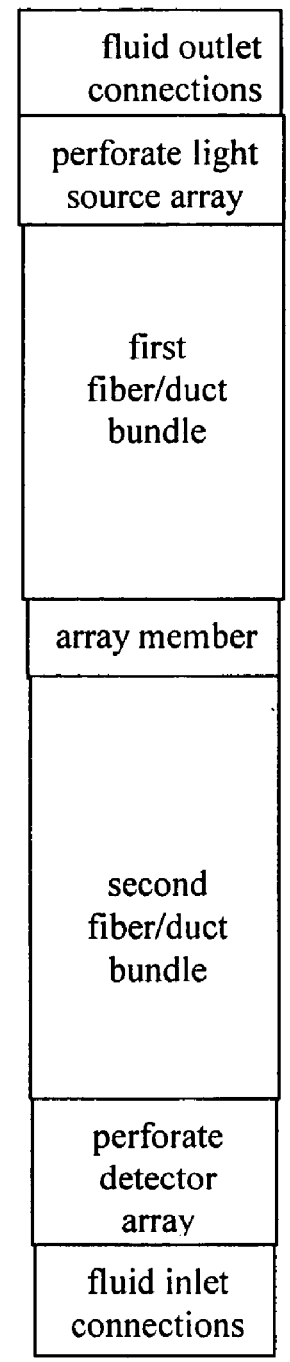
FIG 19
FIG 20

OPTICAL SENSORS

BACKGROUND OF THE INVENTION

Field of the Invention

The present invention relates generally to sensors for the optical testing of gasses, liquids or other fluids, and particularly to sensors capable of observing absorption spectra, fluorescence or Raman spectra, refractive index or other optical characteristics of large numbers of fluid samples (including but not limited to fluid streams) in a small space. Specifically, it is envisioned that the invention may permit the simultaneous testing of up to around 10,000 fluid samples in a column with a cross-sectional area of one square inch (650 mm$^2$).

Other optical characteristics that can be observed include the magnitude of absorbance/transmission or emission at a single wavelength, or at each of a finite number of wavelengths. The invention may be particularly apt for observing changes in one or more optical characteristics of a continuously flowing fluid stream, or for comparing optical characteristics of plural such streams.

By way of example only, the invention may be useful in the detection, identification, assaying and/or screening of large numbers of pharmaceutical candidate substances, of unknown suspected hazardous substances or microorganisms, or of pollutants gathered from many distributed sources.

TECHNICAL BACKGROUND

Optical fibers have been used to bring probe light to a sample to be tested and/or to convey light emerging from the sample to a detector, and a few authors have proposed to make an array of small testing devices using a bundle of fibers; but so far as the applicant is aware, none of them has proposed an efficient way to get a correspondingly large number of fluid samples or streams to the test cells.

SUMMARY OF THE INVENTION

One aspect of the invention is an optical sensor comprising at least one bundle comprising a plurality of optical fibers and a plurality of separate fluid-tight longitudinally extending ducts; and fluid connectors for introducing fluids selectively into at least some of said ducts.

In most cases the ducts and the optical fibers will be in the same bundle (or there will be both ducts and optical fibers in each of the bundles), but in some forms of the invention all the optical fibers may be in one bundle and all the ducts in another, as will become clear later.

The optical fibers may be of the conventional kind comprising a core of relatively high refractive index enclosed in a cladding of lower refractive index, with or without additional outer layers, in which case the ducts may be (a) formed by or accommodated in interstices between the bundled fibers;
(b) bundled with the fibers, typically but not necessarily being of similar cross-sectional dimensions;
(c) in a separate bundle; or possibly more than one of those.

They may also be of the holey kind having a solid core and cladding with longitudinally extending voids, optionally arranged in a periodic array as in photonic crystal fibers; these voids will then be available to form at least some of the ducts, but there may be additional ducts elsewhere.

Most especially, they may be photonic band-gap fibers in which the light guide is formed by a longitudinally extending void "defect" in a photonic crystal structure, the void defects being available to form at least some of the ducts.

Additionally, for some applications, the fibers may be hollow, with or without an inner annular layer of high refractive index within a cladding of lower refractive index; if without, then the fluid to be introduced into the central void of the fiber needs to have a high enough refractive index to itself serve as fiber core.

When conventional fibers are used, their ends may optionally be etched and/or coated to create reflective mirrors. Two such ends when closely aligned to each other can form a Fabry-Perot cavity to increase sensitivity by increasing optical intensity locally.

Another aspect of the invention is an optical sensor comprising at least one bundle comprising a plurality of optical fibers defining a plurality of separate fluid-tight longitudinally extending ducts at least some of which substantially overlap with optical modes of respective said optical fibers;

and fluid connectors for introducing fluids selectively into at least a proportion of said ducts so as to interact with said optical modes over substantially the whole length of said bundle.

This aspect of the invention thus provides for the formation of test cells substantially as long as the bundle, which could be many feet or even a few miles (meters or kilometers) in length, if required, allowing detection and measurement of species present in the fluid in very low concentrations.

Another aspect of the invention is an optical sensor comprising at least one bundle comprising a plurality of optical fibers and a plurality of separate fluid-tight longitudinally extending ducts, the bundle having an end; fluid connectors for introducing fluids selectively into at least some of said ducts; and sealed to said end an array member defining a plurality of cells each in optically transmissive alignment with at least one said fiber and communicating with at least one of said ducts.

Preferably the end of the bundle (or of each bundle) is substantially planar, and the array member is a plate-like member with holes or recesses of appropriate shape(s) and dimensions defining the cells. In some cases the array member is preferably of the same material as the bundle and permanently hermetically sealed to it; in other cases it is preferable and may be necessary for it to be of a resilient material removably held under pressure to maintain the required seal.

A single fiber bundle according to this aspect of the invention be used in a number of ways:

(a) to convey fluid and probe light to respective cells, with an array of light detectors applied more or less directly to the opposite side of the array member; or
(b) to convey fluid to respective cells and carry light from them to remote detectors, all the cells being illuminated by a single light source on the opposite side of the array member;
(c) to convey fluid to respective cells and carry light from them to remote detectors, each of the cells being illuminated by a respective light source of a light source array on the opposite side of the array member; or (d) to convey fluid to respective cells and carry light to them from remote sources and from them to remote detectors, using at least one reflector on the opposite side of the array member.

In each of these cases, the bundle may optionally also convey fluid away after sensing, provided that a cell communicates with at least two of the ducts in the bundle. Otherwise, unless it is acceptable for the fluids to be discarded directly from the array member, a corresponding array of ducts may need to be provided on the other side of the array member.

Alternatively, the sensor includes first and second fiber bundles, one on each side of the array member, so that light passes from a fiber of the first bundle through a test cell formed in the array member to a fiber of the second bundle. In such cases, fluids may be introduced and carried away by ducts in the same or different bundles, as found convenient in a particular case. In some applications, it might be useful to have more than one bundle on one side of the array member, each engaging a part of the cross-sectional area of the single bundle on the other side.

In most cases it is very strongly preferred that at the end, or at each of the ends, at which fluid is to enter or leave a bundle, the optical fibers are connected to an array of optical elements (specifically of light sources, light detectors or reflectors) which is perforate to allow passage of the fluid. A matching bundle of ducts (without optical fibers) can then be connected to the opposite side of the array of optical elements and can be "uptapered" to facilitate the otherwise difficult provision of fluid connections to the individual ducts.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention, and together with the description serve to explain the principles and operations of the invention.

BRIEF DESCRIPTION OF THE DRAWINGS

Each of FIGS. 1–9 is a diagrammatic end view of a typical portion one bundle cross-section that may be used in the present invention.

Each of FIGS. 10–14 is a diagrammatic view of a different form of array member for use in sensors of the invention.

Each of FIGS. 15–20 is a block diagram of a different form of sensor in accordance with the invention.

DETAILED DESCRIPTION OF THE PREFERRED EMBODIMENTS

Figure 1:
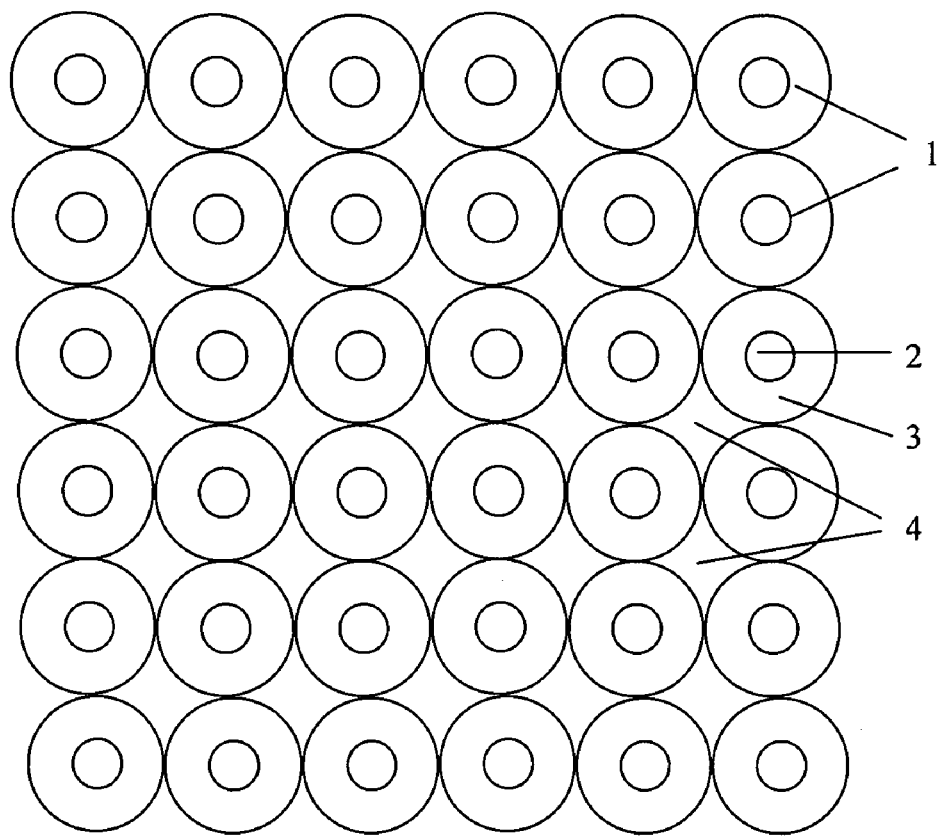

Reference will now be made in detail to the present preferred embodiment(s) of the invention, examples of which are illustrated in the accompanying drawings. Whenever possible, the same reference numerals will be used throughout the drawings to refer to the same or like parts.

FIG. 1 illustrates a first optical fiber bundle structure comprising conventional optical fibers 1 each comprising a core 2 and a cladding 3, arranged on a rectangular grid and fused or otherwise sealed together where they touch, so forming (subject to edge effects) as many interstitial ducts 4 as there are fibers.

Figure 2:
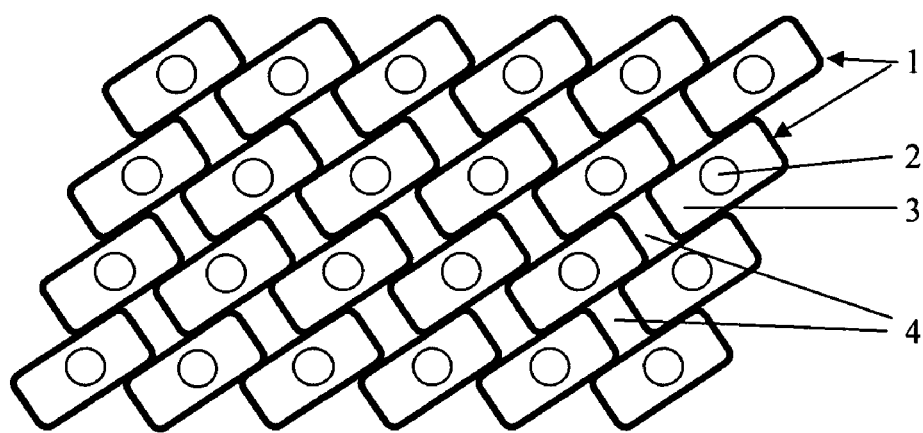

FIG. 2 illustrates an alternative optical fiber bundle structure which is essentially the same except it is formed from fibers of rectangular cross-section.

Figure 3:
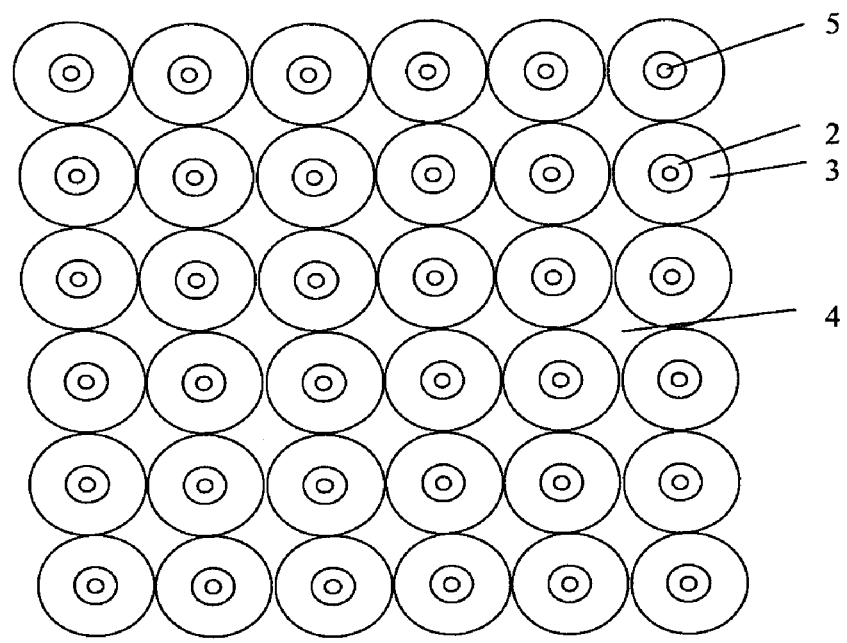

FIG. 3 shows a modified bundle formed of fibers each formed with a central duct 5 within its core, in addition to the interstitial ducts 4. Such fibers can be made without undue difficulty by any of the known fiber-drawing techniques that start from a tubular preform, by adjusting the temperature/tension conditions so that the central void does not quite close. The diameter of the duct 5 in this form of the invention is constrained by the refractive index of the fluid within it and the optical attenuation requirements. In one extreme with the loss requirement very low and the index of refraction close to that of air (n=1), the diameter would have to be close to the wavelength of the light to be transmitted (around 1 μm). In this extreme, the fluid flow would be quite restrictive even in the case of a gaseous fluid and any detected change in fluidic composition would be slow. This form of the invention is more readily used if the fluid supplied to the ducts has a refractive index similar to or higher than that of the core 2, so that it acts as a part of the optical core of the fiber (for example creating a 2-step profile fiber) or as an inner confining core. In some such cases, it may be possible to dispense with a solid optical core and allow the fluid itself to form the core of the fiber.

Figure 4:
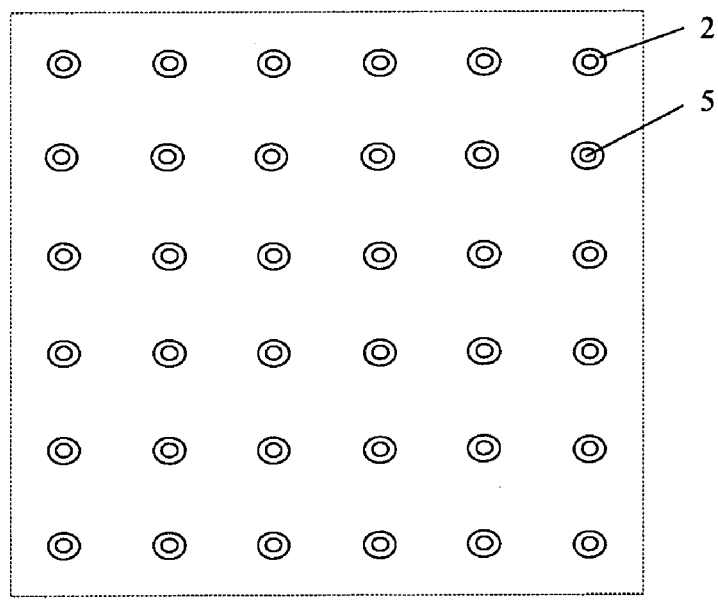

In the bundle of FIG. 4, the interstitial ducts have been eliminated (for example by grinding the fiber preforms to a square section before assembly, or using separate filler rods). If, as shown, this results in a monolithic structure, it will naturally be substantially rigid, whereas other structures illustrated may retain some degree of flexibility.

Figure 5:
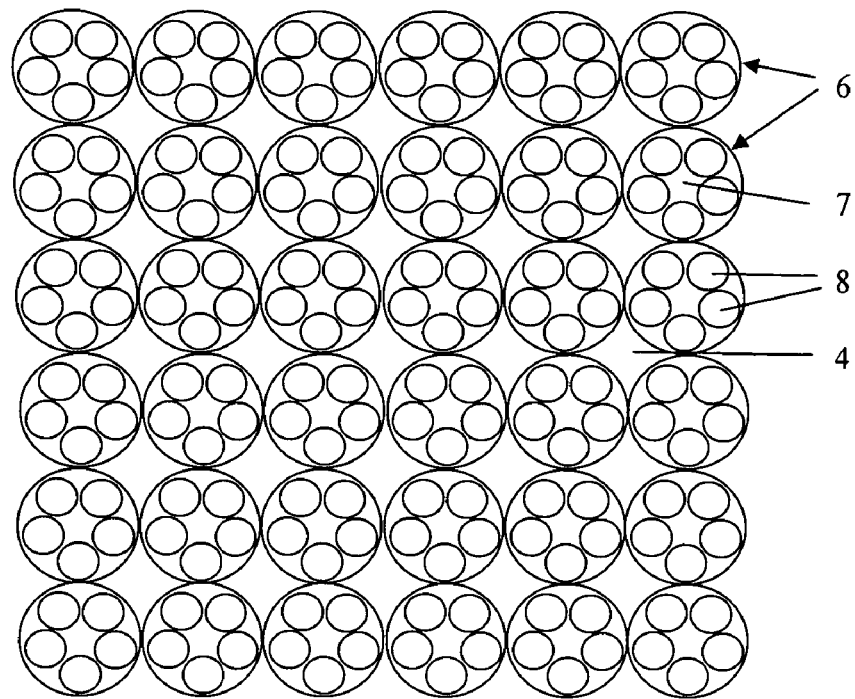

FIG. 5 is a highly diagrammatic representation of an array of holey optical fibers 6, each comprising a solid central core 7 with a cladding that, near the core, consists largely of space defined by a plurality of ducts 8 supported by small amounts of solid material (which for simplicity of drawing has been assumed the same as the material of the core—a solid of lower refractive index may be preferable in practice), in addition to interstitial ducts 4. It will be apparent that the functioning of this type of fiber requires any fluid in ducts 8 to be of low enough refractive index for optical confinement to be maintained, and if fluids in different ducts are not the same, to be sufficiently similar in refractive index to avoid any significant asymmetry, but subject to that limitation they may be used independently of one another.

Figure 6:
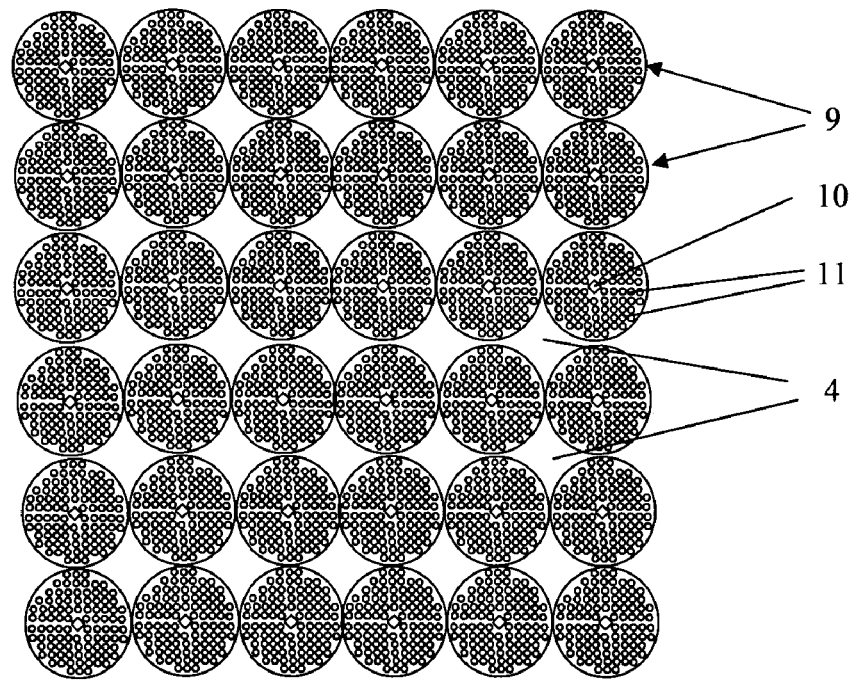

FIG. 6 illustrates an array of photonic band-gap fibers 9 each comprising a central light-transmitting void 10 within a photonic "crystal" comprising a regular array of small passages 11, thus defining two types of ducts in addition to the interstitial ducts 4. It is not usually desirable, in this structure, to introduce fluids into the passages 11 unless its refractive index is close to that of air, as it is liable to decrease the light confinement in the core thereby increasing tunneling loss to the cladding; the void 10 may be used as a duct with relatively few restrictions.

Figure 7:
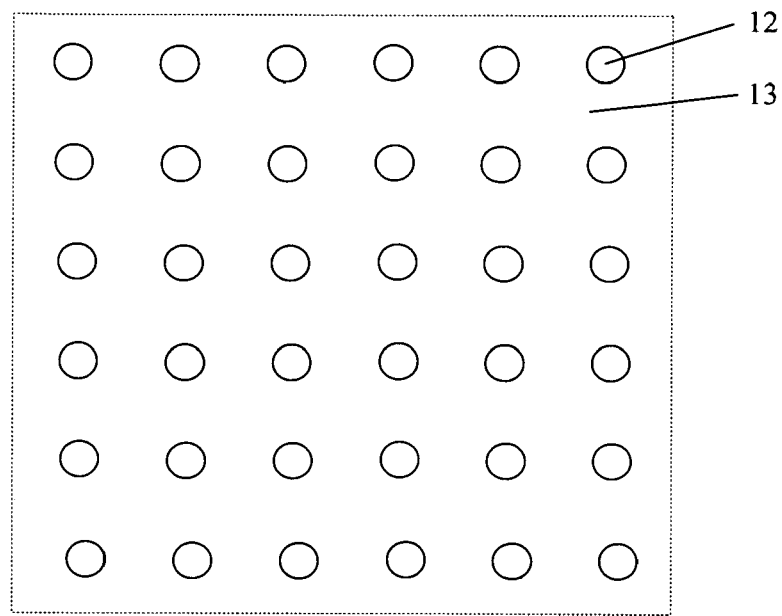

FIG. 7 shows an auxiliary array comprising elements 12 within a matrix 13, and may be taken to represent (a) an optical fiber array without ducts (elements 12 being fiber cores), for use with another array that has ducts (with or without optical fibers); or (b) an array of ducts without fibers (elements 12 then being ducts), for use with another array that has fibers (with or without ducts).

Figure 8:
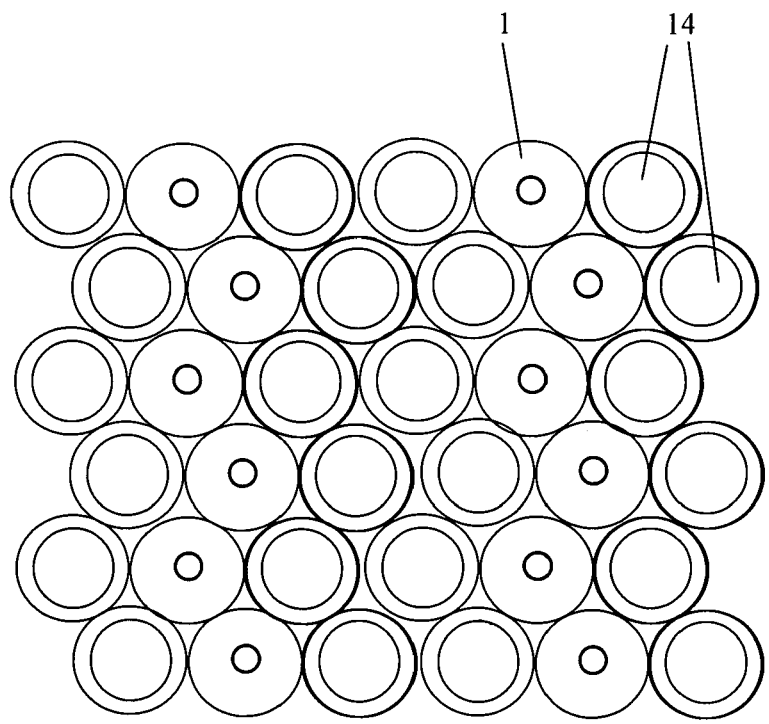
Figure 9:
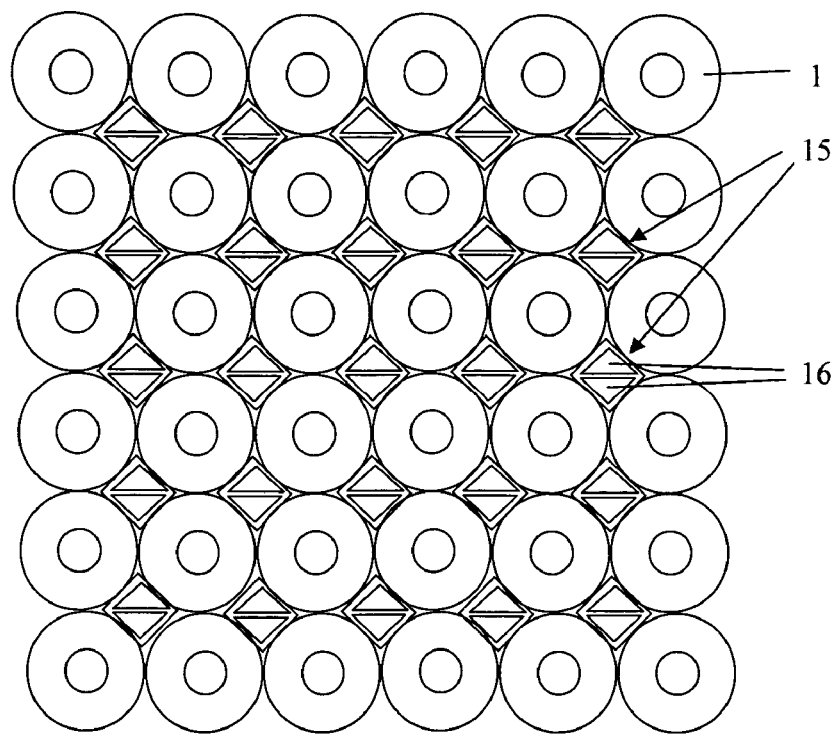

The bundle structures so far described use the fibers alone to define the ducts, and either have equal numbers of fibers and ducts or if there are more ducts than fibers at least some of them are very small compared with the cross-section of the fibers. It will often be desirable to provide two relatively large ducts per fiber, one to supply fluid and the other to remove it, and FIGS. 8 and 9 show two of the many ways in which this may be done. In the construction of FIG. 8, the bundle simply includes separately formed ducts 14, shown as having the same diameter as the fibers 1 so as to bundle neatly with them. The figure also illustrates the fact that the bundle may be close-packed instead of in a rectangular array, as may most of the structures described. The alternative structure of FIG. 9 uses separately formed ducts 15 with two bores 16, 16 and of a size and shape enabling them to be accommodated in the interstices between the fibers 1. Another simple option would be to use two separate, generally triangular ducts in each interstice.

Many embodiments of the invention use generally planar array members with an appropriate pattern of holes and/or recesses, applied to the end of a fiber bundle or sandwiched between two fiber bundles, to interconnect ducts and/or to form cells in which the fluid is to interact with light conducted by the fibers. The pattern of holes and recesses may vary very considerably, depending not only on the structure(s) of the bundle or bundles to which they are to be applied but also on the particular application for which the sensor is to be used. The design process for these is a routine matter within the skills of the art, but a few examples follow to illustrate some approaches.

Figure 10:
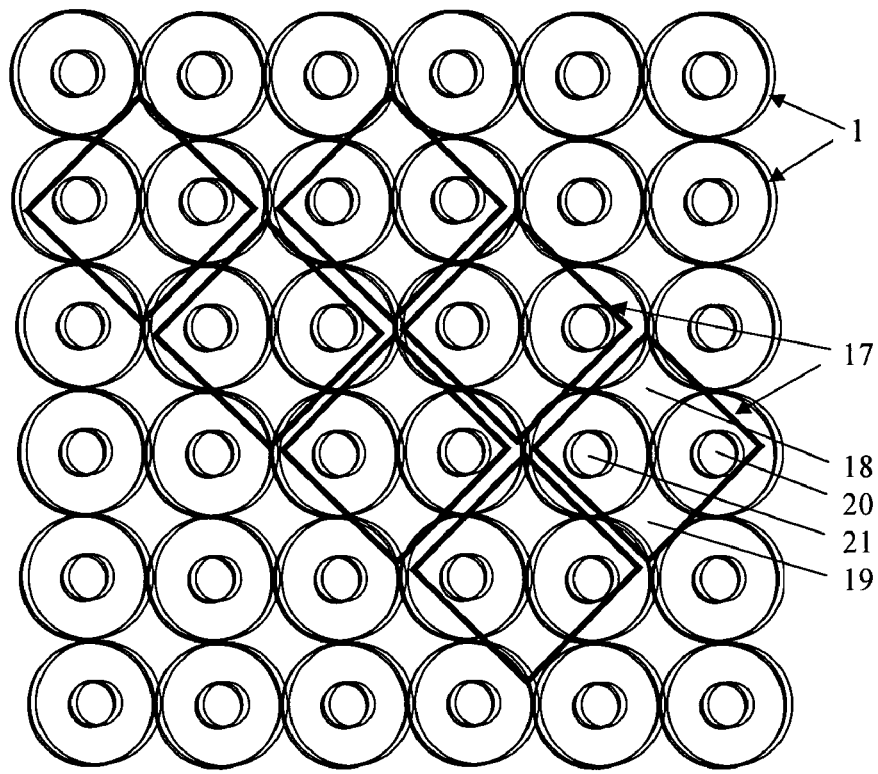

FIG. 10 shows the array of FIG. 1 with a portion of an array member having substantially square, diagonally disposed through-holes (or recesses) 17, each dimensioned to form a cell that communicates with two interstitial ducts 18 and 19 for fluid flow from one of them to the other and communicates optically with two of the optical fibers 20 and 21 to allow the light transmitted by the fibers to interact with the fluid, providing for two measurements on each fluid sample, either duplicates for confirmation or different measurements using light that differs in wavelength, range of wavelengths (if scanned) or other optical characteristics. An alternative arrangement for some types of measurement may use one of the two fibers to introduce probe light and the other to transmit emitted light to a detector.

Figure 11:
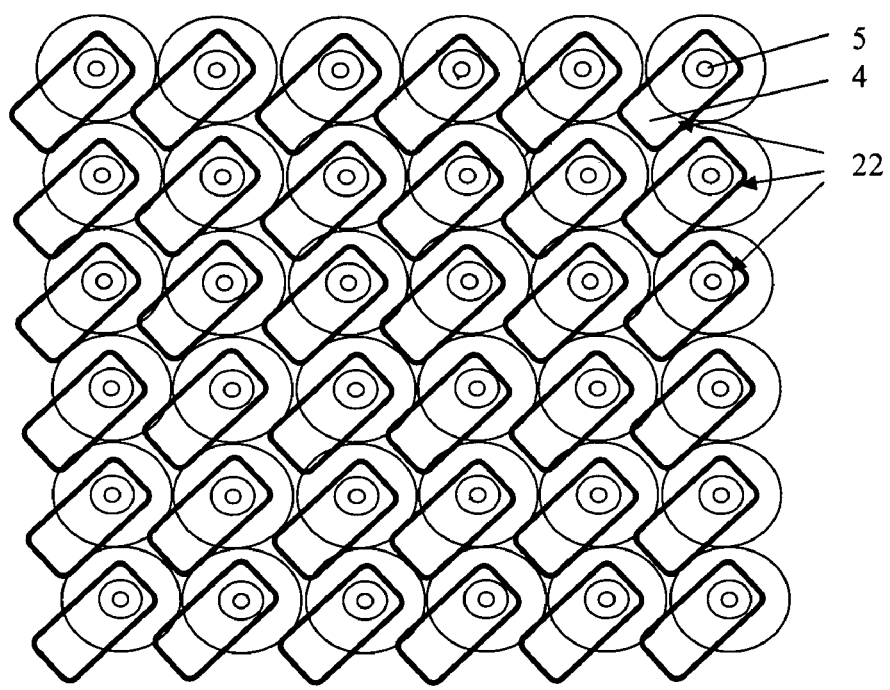
Figure 12:
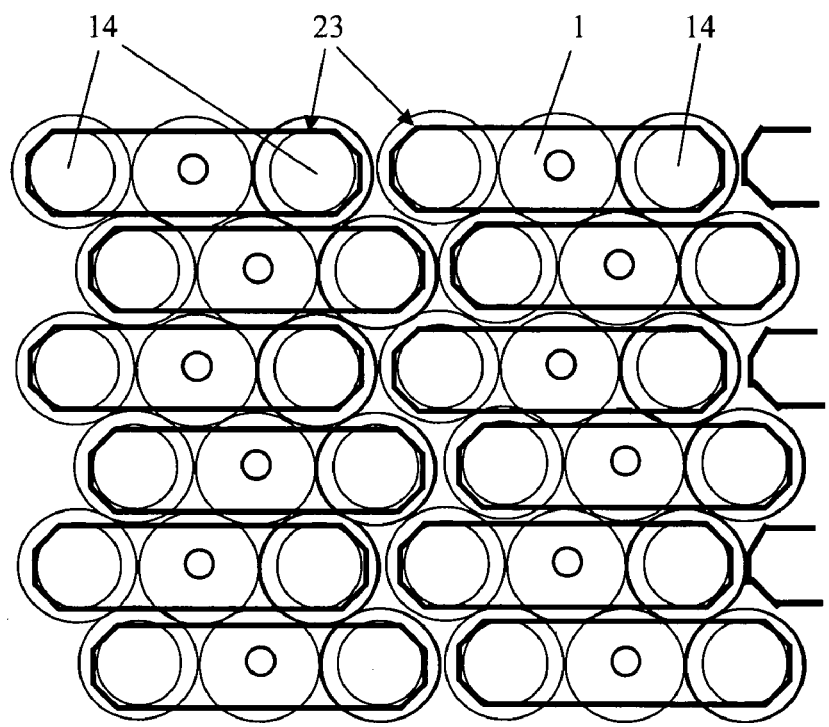

FIG. 11 shows the bundle of FIG. 3 and superimposed on it an array member with oblong recesses 22 each providing communication between an axial duct 5 which is active in the sense that interaction between light and fluid takes place within the duct (whether or not it also takes place in a cell of the array member) and an interstitial one 4 which is passive, and FIG. 12 shows the bundle of FIG. 8 with a somewhat similar array member forming cells 23 that each extend over the end of a respective optical fiber 1 and communicate with two neighboring ducts 14.

Figure 13:
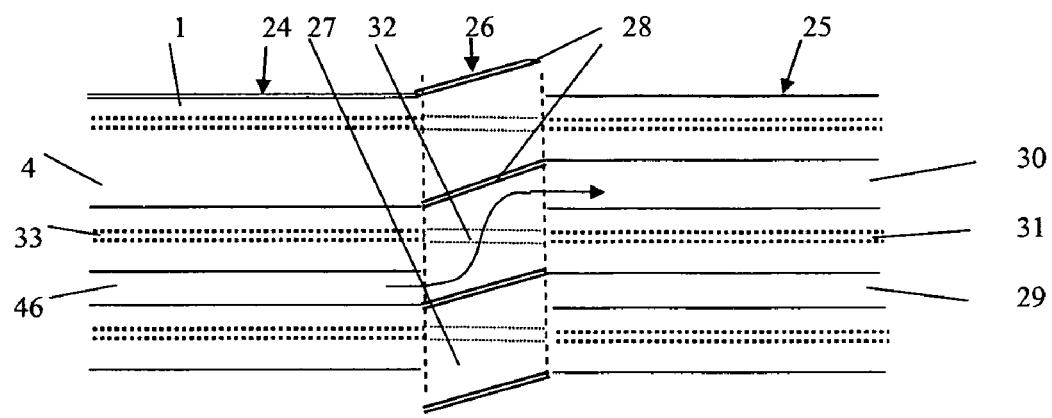
Figure 14:
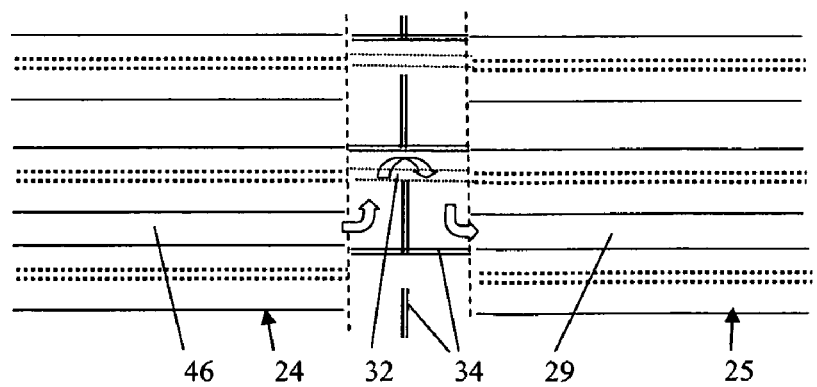

The array members so far described are of substantially uniform cross-section with through-holes, or with the exception of a solid or perforate web at one end (the end remote from the fiber bundle forming or accommodating the ducts they are to communicate with). When possible, this is preferred for simplicity and reliability. However, there may be cases where the sensor includes two bundles with aligned ducts in which it is desirable to provide communication between ducts that are not aligned or to compel an indirect route between cells that are aligned (for example, to ensure the fluid cannot by-pass the optically active parts of a cell). This can be achieved with an array member of appropriate three-dimensional shape. FIGS. 13 and 14 illustrate this, and each of these figures can be considered an option for a sensor based on two bundles 24, 25, each of the kind shown in FIG. 1.

The option of FIG. 13 uses an array member 26, broadly similar in pattern to the one seen in FIG. 10 but in which the openings 27 are through-holes and have end-walls 28 obliquely extending so that any individual duct, for example duct 46, is put into communication not with the duct (for example duct 29) that is aligned with it but with the duct of the other array that is on the opposite side of one of the neighboring fibers (for example duct 30 on the opposite side of fiber 31). In this way, it is ensured that the fluid passes through the active zone 32 axially located between the fibers 31 and 33.

In the alternative structure of FIG. 14, each duct (for example duct 46) does communicate with the duct (29) directly opposite, but the array member 26 includes baffles 34 to ensure that fluid cannot by-pass the active zone 32.

FIGS. 15 through 18 show in block diagram form some principal ways in which sensors in accordance with the invention with a single fiber/duct bundle can be completed and used. In the embodiment of FIG. 15, perforate light source and detector arrays and external connections for the entry and exit of fluid are all located at the end of the bundle remote from the array member, and the sensor is completed by a reflector on the opposite side of the array member. This is a desirable arrangement, for example, if the fluid might damage the faces of the light sources or detectors, or be contaminated by contact with them, but may require additional optical components (for example microlenses, circulators, wavelength-division multiplexer/demultiplexers or splitter-couplers) to ensure correct optical routing and efficient coupling to and from the fibers. In the embodiment of FIG. 16, a detector array (for example a photodiode array) is applied directly to the side of the array member remote from the bundle; this simplifies the optical connections. This arrangement can be reversed, as illustrated by FIG. 17, in which a laser array or other light source is directly applied to the array member and a detector array at the remote end of the fiber. Vertical-cavity side-emitting laser arrays (VCSEL arrays) may be particularly convenient for this application, but laser diodes and amplified spontaneous emission sources can also be used; in a few instances, it may be possible to use a single large-area source, even an incandescent lamp, to illuminate the whole array. FIG. 18 illustrates the possibility that the fluid, rather than being returned through ducts in the bundle, may exit from the side of the array member. This may be appropriate, simplifying and convenient for example if the fluid is air or another ambient fluid, for instance being monitored for pollution, and the observations being made will not be jeopardized by mixing of fluid from different streams after they have passed through the test cells.

FIG. 19 similarly illustrates one way of constructing and using a sensor in accordance with the invention based on one bundle of fibers without ducts, and one bundle of ducts without fibers. A perforate reflector is used in contact with the array member with light source and detector arrays both located at the far end of the fiber bundle and fluid inlet and outlet at the far end of the duct bundle.

FIG. 20 illustrates one arrangement using two bundles each containing both fibers and ducts; the light source array and fluid outlet are located at one end and the detector array and fluid inlet at the other. Naturally it is possible to reverse the relative direction of fluid flow if desired. It is also possible, if it should be desired, to have opposite directions of fluid flow in different ducts, and/or different directions of light propagation in different fibers.

Bundles of glass fibers and/or glass ducts for use in the invention may be made by known techniques based on the assembly and co-drawing of simple component shapes and/or extrusion of more complex ones. The end of the bundle to contact the array member may in some cases be tapered to a smaller (or larger) size than its other end. Where the array member is also of glass, it may be made of a size corresponding to an intermediate draw stage and bonded to the bundle or bundles before final draw.

It will be apparent that in some cases making optical and fluid connections to the sensor of the invention may be a challenging task. As already indicated, it is very much preferred, when possible, to simplify it by using a perforate array of optical elements at one or both ends of the sensor where fluid connections are to be made. Such array may be applied to the array member or direct to the end of a bundle, as appropriate for the particular sensor, and may comprise light sources, light detectors or reflectors, or in principle more than one of those, though in practice the inclusion of both light sources and light detectors may require separate perforate substrates stacked one on the other (and might in consequence of the thickness of the substrate nearer to the fiber bundle need microlenses or other optical collimating means to insure satisfactory optical coupling to the optical elements on the other substrate).

Figure 21:
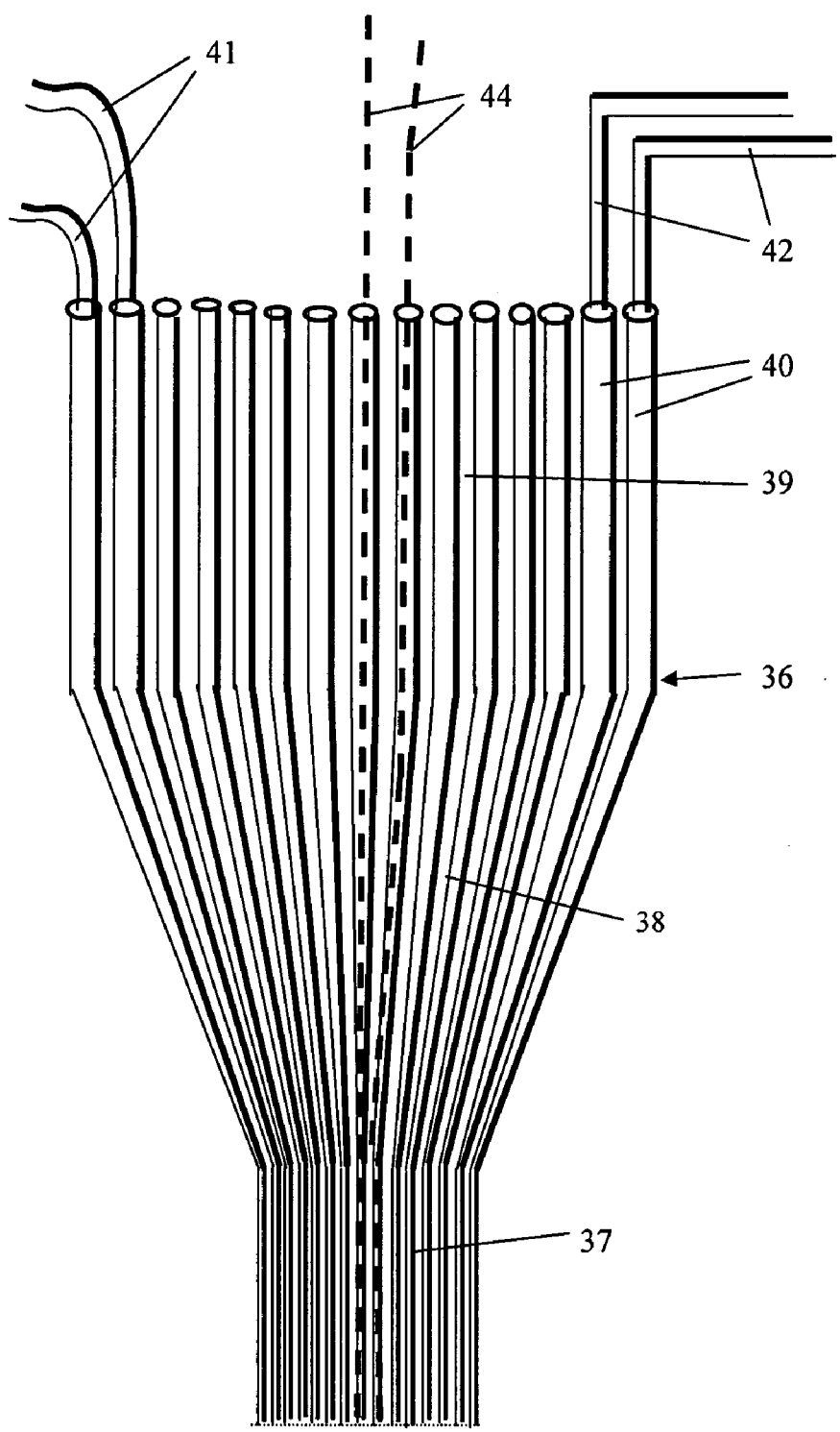
FIG. 21 is a diagrammatic representation of a part of a sensor in accordance with the invention illustrating exemplary ways of making external connections to it.

When the fluid connections have been separated from the optical paths in that way, it becomes relatively easy to direct them as desired, because it is readily possible to apply to the side of the substrate furthest from the bundle an auxiliary bundle comprising ducts only (meaning only without fibers) which is tapered so as to match the dimensions of the perforate array at one end and to be much enlarged at the other end. Such auxiliary bundles can be made, inter alia, by substantially the same stack-and-draw technique as described for making the main bundles, but fully drawing down over only part of its length. FIG. 21 is a diagrammatic representation of such a tapered auxiliary bundle 36, for clarity showing only a few ducts and greatly foreshortening the bundle. The narrow part 37 may be substantially the same in structure as the bundle illustrated as interpretation (b) of FIG. 7 and used, for example, in the sensor illustrated by FIG. 19; the remainder is identical in structure, except only that it gradually and proportionately increases in transverse dimensions in the middle section 38 until at its wide end 39 the ducts 40 are large enough to facilitate connection to individual flexible or curved tubes 41, or tubes 42 with integral or separate angles, as appropriate and convenient for the particular application.

There will be instances where the use of a matching array of light sources or light detectors at an end of the bundle is not possible, for example because light of the required characteristics cannot be obtained from a semiconductor light source but requires—say—a gas laser, or because the relevant characteristics of the light cannot be detected by a semiconductor photodetector but may require—for example—a photomultiplier device. As an alternative to sealing individual tubes and individual optical fibers to the end of the bundle by precision microengineering techniques is to bond to the end of the bundle an auxiliary bundle of ducts, exactly like the one already described with reference to FIG. 21 but with a duct aligned with each fiber end, in addition to those aligned with ducts. Prepared ends of optical fibers 44 can then be inserted into wide ends of the appropriate ducts and advanced until they substantially abut and couple to the fibers in the bundle.

APPLICATION EXAMPLES

A sensor in accordance with the invention using the fiber/duct bundle of either FIG. 3 or FIG. 4 or FIG. 5, suitably (in each case and among other possibilities) with the array member shown in FIG. 11 and the arrangement of FIG. 16 may be used to make a compact sensor for continuously monitoring air at multiple positions in a building and/or about an outdoor area for multiple contaminants (whether accidental or malicious). The fiber bundle is of substantial length, for example of the order of 25 yards (or meters) to allow sensitivity to detect low levels of contamination. Air from each sampling point is ducted to one end of the fiber bundle, and there distributed to the ducts within the active part of the fiber, each sample entering a different plurality of the fibers. Different light source/detector regimes are applied to individual fibers in that plurality, though not necessarily to all of them as duplicated testing may be desirable for confirmation of results. For example, the light sources may differ in wavelength or may scan through different wavelength ranges and the detectors may be set up to measure light absorption, scattering, fluorescence, scintillation (for which no light input is needed) or other effects that may be characteristic of different chemical, radiological or biological pollutants. If the nature of potential pollutants makes it necessary or desirable, chemical reagents may be introduced into individual fluid streams (or groups of them) to permit or facilitate detection.

In another application, the bundle and array member of FIG. 10 may be used in the arrangement of FIG. 15 for multiple ligand binding assays in pharmaceutical research: the reflector is to be interchangeable and to be printed with a pattern (for example stripes) of different immobilized receptor molecules, and ligand solutions are applied through appropriate ducts in the fiber bundle so that each ligand is presented to each of the receptors, with binding being detected and if desired quantified in respect of extent and/or reaction rate by optical observation. To the extent the nature of the assay allows it, it may be preferable for the materials to be evaluated (for example, unknown materials to be identified) to be immobilized in the printed pattern and the standard reagents with which they are to be tested to be supplied in solution via the ducts.

Several potential applications may use the fiber bundle of FIG. 1 with the array member of FIG. 14 in the arrangement of FIG. 20 with a chemically or biochemically significant coating on the face of the fiber bundle 24.

In one subgroup of these applications, the coating is a primer coating (many examples of which are known in the biochemical arts) for facilitating the subsequent printing and binding of DNA, protein, antibody or other biochemical samples. Reagents for identifying and/or assaying the samples are supplied through the ducts, and the reaction on the surface observed optically by measurement of absorption, florescence or refractive index change.

In another subgroup of applications, the surface coating is a catalyst for a characteristic reaction of a substance to be detected, whereby a change of absorption may enable detection when direct spectroscopic observation may be obstructed by other substances present in the fluid stream.

Where the nature of the fibers in a bundle and the observation technique to be used make it possible and appropriate, the ends of the fibers may be selectively etched to form concave recesses that can be coated with a reflector (if necessary) to form Fabry-Perot cavities to increase optical path length in the cells formed by the array member and so detection sensitivity. For example, typical germanium-doped silica multimode fibers of the type having a graded refractive index with an α value of 2 is readily etched to form cavities with longitudinal cross-section close to a parabola, which is an ideal shape for this purpose.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

Any discussion of the background to the invention herein is included to explain the context of the invention. Where any document or information is referred to as "known", it is admitted only that it was known to at least one member of the public somewhere prior to the date of this application. Unless the content of the reference otherwise clearly indicates, no admission is made that such knowledge was expressed in a printed publication, nor that it was available to the public or to experts in the art to which the invention relates in the US or in any particular country (whether a member-state of the PCT or not), nor that it was known or disclosed before the invention was made or prior to any claimed date. Further, no admission is made that any document or information forms part of the common general knowledge of the art either on a world-wide basis or in any country and it is not believed that any of it does so.

What is claimed is:

1. An optical sensor comprising
at least one bundle comprising a plurality of optical fibers and a plurality of fluid-tight longitudinally extending ducts wherein said ducts are disposed so as to be in optical communication with said optical fibers substantially over the length of said optical fibers;
and fluid connectors for introducing fluids selectively into at least some of said ducts.

2. The optical sensor of claim 1 wherein said optical fibers each comprise a core of relatively high refractive index enclosed in a cladding of lower refractive index.

3. The optical sensor of claim 2 wherein said ducts are formed by interstices between the bundled fibers.

4. The optical sensor of claim 2 wherein said ducts are accommodated in interstices between the bundled fibers.

5. The optical sensor of claim 2 wherein said ducts are bundled with said fibers.

6. The optical sensor of claim 2 wherein ends of said fibers are etched to form Fabry-Perot cavities.

7. The optical sensor of claim 1 wherein each of said fibers comprises a core that is solid and a cladding that has longitudinally extending voids which form at least some of said ducts.

8. The optical sensor of claim 1 wherein said fibers are photonic band-gap fibers in which a light guide is formed by a longitudinally extending void "defect" in a photonic crystal structure, which defects form at least some of said ducts.

9. The optical sensor of claim 1 wherein said fibers are hollow.

10. An optical sensor comprising
at least one bundle comprising a plurality of optical fibers and a plurality of fluid-tight longitudinally extending ducts wherein said ducts are disposed so as to be in optical communication with said optical fibers substantially over the length of said optical fibers, at least some of which substantially overlap with optical modes of respective said optical fibers;
and fluid connectors for introducing fluids selectively into at least a proportion of said ducts so as to interact with said optical modes over substantially the whole length of said bundle.

11. The optical sensor of claim 10 wherein each of said fibers comprises a core that is solid and a cladding that has longitudinally extending voids which form at least some of said ducts.

12. The optical sensor of claim 10 wherein said fibers are photonic band-gap fibers in which a light guide is formed by a longitudinally extending void "defect" in a photonic crystal structure, which defects form at least some of said ducts.

13. The optical sensor of claim 10 wherein said fibers are hollow.

14. An optical sensor comprising
at least one bundle comprising a plurality of optical fibers and a plurality of fluid-tight longitudinally extending ducts wherein said ducts are disposed so as to be in optical communication with said optical fibers substantially over the length of said optical fibers the bundle having an end;
fluid connectors for introducing fluids selectively into at least some of said ducts; and sealed to said end an array member defining a plurality of cells each in optically transmissive alignment with at least one said fiber and communicating with at least one of said ducts.

15. The optical sensor of claim 14 wherein said end of the bundle is substantially planar and the array member is a plate-like member with formations selected from holes and recesses forming said cells.

16. The optical sensor of claim 15 wherein said array member is of the same material as said bundle and permanently hermetically sealed thereto.

17. The optical sensor of claim 15 wherein said array member is of a resilient material removably held under pressure.

18. The optical sensor of claim 14 comprising a single fiber bundle connected to convey fluid and probe light to respective said cells and further comprising an array of light detectors applied to the opposite side of said array member.

19. The optical sensor of claim 14 comprising a single fiber bundle connected to convey fluid to respective said cells and carry light from them to remote detectors, all the cells being illuminated by a single light source on the opposite side of said array member.

20. The optical sensor of claim 14 comprising a single fiber bundle connected to convey fluid to respective said cells and carry light from them to remote detectors, each of the cells being illuminated by a respective light source of a light source array on the opposite side of said the array member.

21. The optical sensor of claim 14 comprising a single fiber bundle connected to convey fluid to respective cells and carry light to them from remote sources and from them to remote detectors, and further comprising at least one reflector on the opposite side of said array member.

22. The optical sensor of claim 14 wherein each said cell communicates with at least two of the ducts in the bundle respectively for conveying fluid to and from said cell.

23. The optical sensor of claim 14 further comprising a corresponding array of ducts on the other side of the array member.

24. The optical sensor of claim 15 further comprising at one of its ends a matching perforate array of optical members selected from the group consisting of light sources, light detectors and reflectors, sealed to said end and providing a through passage for each said duct.

25. The optical sensor of claim 24 having a said perforate array of optical members at each of its ends.

26. The optical sensor of claim 24 further comprising an auxiliary bundle of ducts which is tapered from a narrow first end matching said perforate array and providing ducts each communicating via said perforate array with one of said separate longitudinally extending ducts to a large end facilitating connections for fluid flow.

27. The optical sensor of claim 14 further comprising an auxiliary bundle of ducts which is tapered from a narrow first end matching said perforate array and sealed to it to provide
   a first plurality of ducts each communicating via said perforate array with one of said separate longitudinally extending ducts
   and a second plurality of ducts each aligned with a said optical fiber to a large end facilitating (a) the connection of individual ducts for fluid flow to each duct of said first plurality and (b) the connection of individual optical fiber ends with said optical fibers by insertion into the ducts of said second plurality so as to substantially abut said optical fibers.

28. An optical sensor comprising first and second fiber bundles, each said bundle comprising a plurality of optical fibers and a plurality of fluid-tight longitudinally extending ducts wherein said ducts are disposed so. as to be in optical communication with said optical fibers substantially over the length of said optical fibers, each bundle having an end;
   fluid connectors for introducing fluids selectively into some of said ducts and receiving fluids from others of said ducts;
   and sealed between said bundles in contact with each said end an array member defining a plurality of cells;
   each said cell being in optically transmissive alignment with at least one selected said fiber of each said bundle and communicating with at least two selected said ducts.

29. The optical sensor of claim 28 wherein each said cell communicates with a first said duct in said first optical bundle and a second said duct in said second optical bundle, said first duct and said second duct being axially aligned with each other.

* * * * *

UNITED STATES PATENT AND TRADEMARK OFFICE
CERTIFICATE OF CORRECTION

PATENT NO.       : 7,129,510 B2                     Page 1 of 1
APPLICATION NO.  : 10/978134
DATED            : October 31, 2006
INVENTOR(S)      : Alan Frank Evans et al.

It is certified that error appears in the above-identified patent and that said Letters Patent is hereby corrected as shown below:

*Col.*   *Line*

12       9       delete . (period) between so and as

Signed and Sealed this

Sixth Day of March, 2007

JON W. DUDAS
*Director of the United States Patent and Trademark Office*